United States Patent [19]

Kopel

[11] 4,363,326
[45] Dec. 14, 1982

[54] ULTRASONIC APPARATUS FOR NEEDLE INSERTION

[75] Inventor: LeRoy Kopel, Tempe, Ariz.

[73] Assignee: Advanced Diagnostic Research Corporation, Tempe, Ariz.

[21] Appl. No.: 218,512

[22] Filed: Dec. 22, 1980

[51] Int. Cl.³ .............................................. A61B 10/00
[52] U.S. Cl. .................................. 128/660; 128/24 A
[58] Field of Search ................................. 12/660, 24 A

[56] References Cited

U.S. PATENT DOCUMENTS

| | | | |
|---|---|---|---|
| 3,857,387 | 12/1974 | Shock | 128/24 A |
| 3,902,495 | 9/1975 | Weiss et al. | 128/24 A |
| 4,058,114 | 11/1977 | Soldner | 128/660 |
| 4,289,139 | 9/1981 | Enjoji | 128/660 |

Primary Examiner—Kyle L. Howell
Assistant Examiner—Daniel Burke

Attorney, Agent, or Firm—Christie, Parker & Hale

[57] ABSTRACT

Ultrasonic interrogating apparatus for needle insertion has an array of ultrasonic transducers, electronics for exciting the transducers to ultrasonic emission and receiving ultrasonic echoes therefrom, a housing for the electronics having first and second ends, and a display for presenting the received echoes. The array of transducers is seucred to the electronics housing in laterally offset relationship therefrom. The passage extends through the array of transducers without extending through the electronics housing. A needle is inserted through the passage in the transducer array for the purpose of aspiration or biopsy. The passage comprises a longitudinal slot converging from end to end and a transverse slot extending laterally for the entire length of the longitudinal slot from the longitudinal slot to the side surface of the array.

6 Claims, 4 Drawing Figures

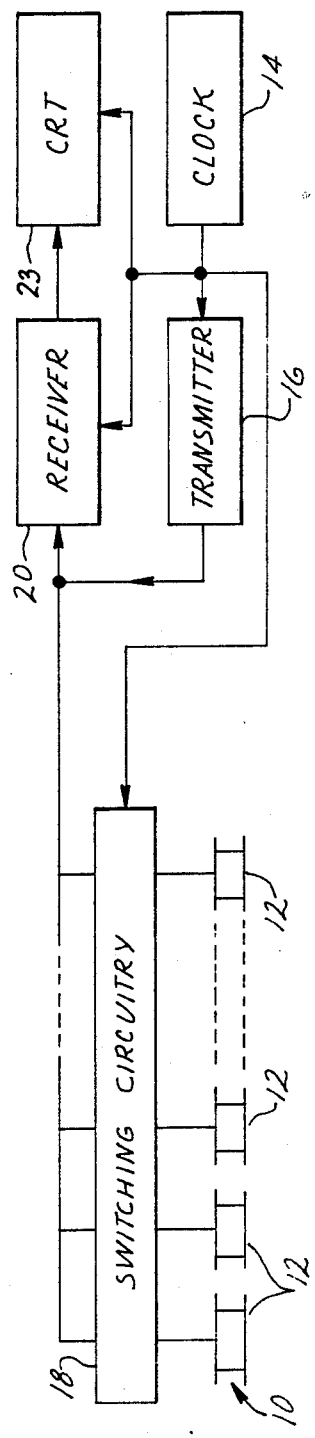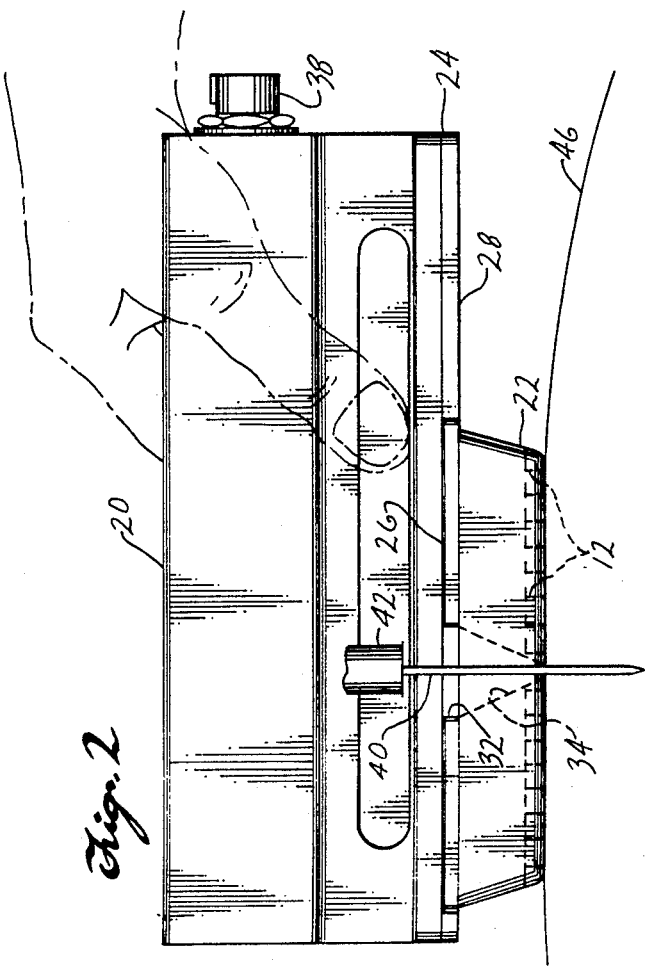

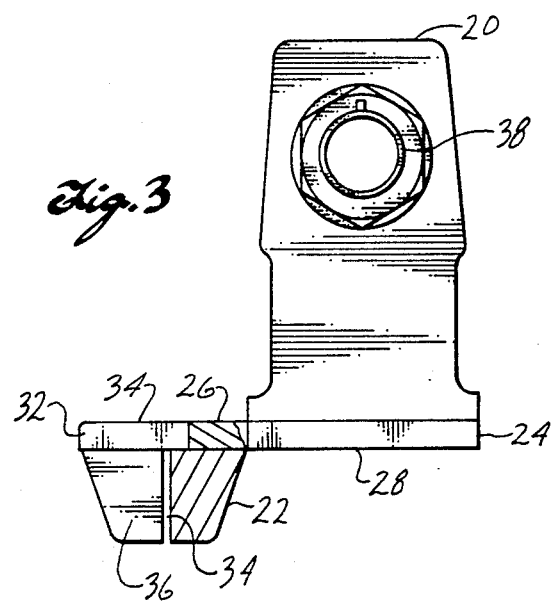
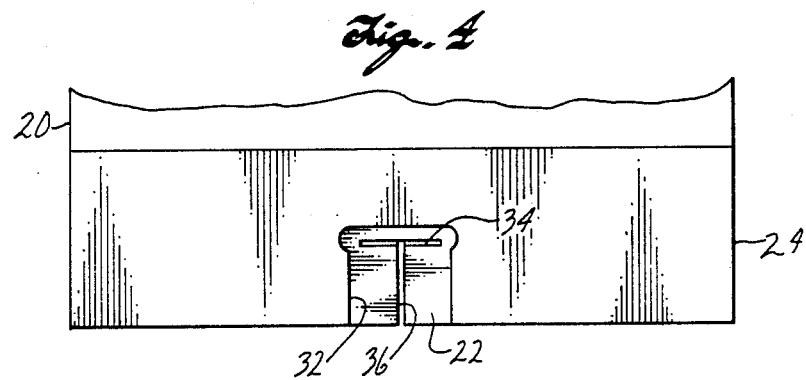

ULTRASONIC APPARATUS FOR NEEDLE INSERTION

BACKGROUND OF THE INVENTION

This invention relates to ultrasonic interrogation and, more particularly, to ultrasonic interrogating apparatus used for needle insertion.

Real-time ultrasonic scanners are commonly used in the medical field for non-invasive examination of the human body. Such a scanner produces on the screen of a cathode ray tube a two-dimensional, cross-sectional image of the body region being interrogated by an array of ultrasonic transducers. The transducer array is packaged in a hand-held unit. The transducers are mounted on one end of a grip that fits in the palm of the user's hand, so his fingers and thumb can grasp the sides of the unit. Sometimes, the hand grip also serves as the housing for the electronics.

Ultrasonic scanners are also used to aid needle insertion during medical procedures such as aspiration of fluid from an interior body region or biopsy performance. In such cases, the scanner interrogates the affected body region while the needle is being inserted, thereby producing on the screen of the cathode ray tube an image representing the relative positioning between the needle and the internal body structures of the region. A slot or hole extends through the hand grip from end to end and through the center of the transducer array for insertion of the needle. The syringe attached to the needle is positioned adjacent to the user's hand at the end of the hand grip and the needle extends all the way through the hand grip from end to end and the transducer array into the body of the patient.

SUMMARY OF THE INVENTION

According to the invention, ultrasonic interrogating apparatus for needle insertion has an array of ultrasonic transducers, a hand grip, electronics for exciting the transducers to ultrasonic emission and receiving ultrasonic echoes therefrom, and a display for presenting the received echoes. The array of transducers is secured to the hand grip in laterally offset relationship therefrom to form a hand-held unit. Preferably, but not necessarily, the hand grip serves as a housing for the electronics. A passage extends through the array of transducers without extending through the hand grip. A needle is inserted through the passage in the transducer array for the purpose of aspiration or biopsy. Because the needle does not pass through the hand grip, it can be shorter in length than heretofore possible and the user's hand on the grip does not interfere with the needle inserting procedure.

BRIEF DESCRIPTION OF THE DRAWINGS

The features of a specific embodiment of the best mode contemplated of carrying out the invention are illustrated in the drawings, in which:

FIG. 1 is a schematic block diagram of an ultrasonic scanner;

FIG. 2 is a side elevation view of a hand-held unit incorporating the components of FIG. 1, and a needle for aspiration or biopsy;

FIG. 3 is an end partial sectional view of the unit of FIG. 2 without the needle; and FIG. 4 is a top view of a part of the unit of FIG. 2.

DETAILED DESCRIPTION OF THE SPECIFIC EMBODIMENT

In FIG. 1 an ultrasonic transducer array 10 comprises a plurality of piezoelectric crystals 12 arranged in a straight row. Under the control of a clock 14, a transmitter 16 generates pulses that excite the crystals of array 10. The pulses from transmitter 16 are distributed to selected crystals of array 10 by switching circuitry 18, which is also controlled by clock 14. The selectively excited crystals of array 10 each emit a burst of ultrasonic energy and the resulting echoes are delivered by switching circuitry 18 to a receiver 20. Receiver 20 produces a video signal that drives a display device in the form of a cathode ray tube (CRT) 23. Clock 14 also controls cathode ray tube 23 and swept gain control circuitry in receiver 20. The described apparatus comprises a conventional linear real-time ultrasonic scanner of the type described in Bom's U.S. Pat. No. 3,789,833 or Wilcox's U.S. Pat. No. 3,881,466, the disclosures of which are incorporated herein fully by reference.

In FIGS. 2, 3, and 4 is a hand-held unit in which a number of the components of FIG. 1 are packaged. The unit comprises an elongated, electronics housing 20 in which clock 14, transmitter 16, switching circuitry 18, and receiver 20 are packaged, an elongated transducer housing 22, and a mounting plate 24. Electronics housing 20 also serves as a hand grip for the unit. Plate 24 has opposite mounting surfaces 26 and 28. One end of electronics housing 20 is secured to surface 26 by fasteners, not shown. One end of transducer housing 22 is secured to surface 28 by means not shown. Crystals 12 are arranged in housing 22 so as to emit ultrasonic energy from the other end thereof. The arrangement of crystals 12 in housing 22, which is longitudinally aligned with housing 22, is represented by hidden lines in FIG. 2. (Generally, many more crystals, e.g., 64, would be employed in array 10 than represented in FIGS. 1 and 2.) Housing 22 could be a molded plastic body that encapsules crystals 12 and their connecting cables. One or more channels (not shown) are formed in plate 24 to carry cable bundles form the crystals in housing 22 to the switching circuitry in housing 20. As best illustrated in FIG. 3, transducer housing 22 is laterally offset from electronics housing 20. A rectangular opening 32 is formed in plate 24 over the middle of transducer housing 22. A longitudinal slot 34 is formed in housing 22, converging from end to end. A transverse slot 36, which intersects the middle of slot 34, is also formed in housing 22. Slot 34 is preferably aligned laterally with the beam center of crystals 12. It converges from the end of housing 22 secured to plate 24 to the width of slot 36 at the other end of housing 22. Slot 36 is preferably at the middle of the row of crystals 12, i.e., the same number of crystals 12 lie on each side of slot 36. Slot 36 also extends for the entire length of slot 34, i.e., from end to end of housing 22, and laterally from slot 34 to the side surface of housing 22, thereby providing access sideways to slots 34 and 36 from the exterior of the unit. Alternatively the passage through the housing could be in the form of a hole. A plug 38 is mounted on one end of housing 120 for connection of the cable leading to cathode ray tube 22, and if desired, other electronic apparatus.

As depicted in FIG. 2, the end of housing 20 opposite plate 24 fits in the palm of the hand of the user and the user's fingers and thumb grip the sides of housing 20. A needle 40 connected to a syringe 42 is inserted into slot 34 from the end of housing 22 attached to plate 24. As needle 40 enters the patient, represented by reference numeral 46, needle 40 appears on the screen of cathode ray tube 22 in proper spatial relationship with the interrogated body structures. Syringe 42 lies above plate 24, i.e., on the side of plate 24 opposite transducer housing 22, needle 40 and syringe 42 are laterally offset from and adjacent to electronics housing 20.

The convergence of slot 34 permits the entrance angle, and therefore the location of, needle 40 to be changed without moving the unit. The extension of slot 36 to the side surface of housing 22 permits the unit to be disengaged entirely from needle 40 without needle removal from the patient.

In summary, plate 24 serves to connect transducer housing 22 to the end of electronics housing 20 in laterally offset relationship. This enables a needle to be inserted through a passage in transducer housing 22 without passing through electronics housing 20, which permits use of a much shorter needle than heretofore. Further, the user's hand does not interfere with the insertion of the needle, because it is laterally offset therefrom.

The described embodiment of the invention is only considered to be preferred and illustrative of the inventive concept; the scope of the invention is not to be restricted to such embodiment. Various and numerous other arrangements may be devised by one skilled in the art without departing from the spirit and scope of this invention. For example, the invention could be practiced in a sector scanner of the type disclosed in an article by J. C. Somer in *Ultrasonics*, July 1968, pages 153-159, entitled "Electronic Sector Scanning for Ultrasonic Diagnosis."

What is claimed is:

1. Ultrasonic interrogating apparatus comprising:
   an array of ultrasonic transducers;
   electronic means for exciting the transducers to ultrasonic emission and receiving ultrasonic echoes from the transducers;
   means for connecting said transducers with said electronic means;
   means for displaying the ultrasonic echoes received from the transducers;
   a hand grip having a first end and a second end;
   means for attaching the array of transducers to the hand grip in offset relationship from the first end thereof;
   a passage extending through the transducer array without extending through the hand grip; and
   a needle slidably inserted into the passage.

2. The apparatus of claim 1, in which the passage comprises a longitudinal slot converging in a direction away from the first end of the hand grip.

3. The apparatus of claim 2, in which the passage additionally comprises a transverse slot extending laterally from the longitudinal slot to the side surface of the transducer arrary to provide lateral access to the longitudinal slot.

4. The apparatus of claim 3, in which the hand grip contains at least some of the electronic means.

5. An ultrasonic scanner comprising:
   a straight row of ultrasonic transducers;
   an elongated transducer housing containing the transducers;
   electronic means for exciting the transducers to ultrasonic emission and receiving ultrasonic echoes from the transducers,
   an elongated hand grip;
   a base plate having first and second opposite mounting surfaces;
   means for securing the hand grip to the first mounting surface;
   means for securing the transducer housing to the second mounting surface in laterally offset parallel relationship to the hand grip; and
   a passage extending through the mounting plate and the transducer housing without passing through the hand grip.

6. The apparatus of claim 5, in which the hand grip serves as a housing for the electronics means.

* * * * *